United States Patent

Gautherin et al.

Patent Number: 5,114,231
Date of Patent: May 19, 1992

[54] SPECTROSCOPIC ANALYSIS DEVICE

[75] Inventors: Jean-Claude Gautherin; Henri Zegre, both of Sucy en Brie, France

[73] Assignee: Instrument SA, France

[21] Appl. No.: 577,891

[22] Filed: Sep. 5, 1990

[30] Foreign Application Priority Data

Sep. 5, 1989 [FR] France ............... 89 11607

[51] Int. Cl.$^5$ ............................................. G01J 3/20
[52] U.S. Cl. ...................................... 356/328; 356/334
[58] Field of Search ............... 356/305, 326, 328, 331, 356/332, 334

[56] References Cited

U.S. PATENT DOCUMENTS

| | | | |
|---|---|---|---|
| 4,027,975 | 6/1977 | Turner et al. | 356/334 |
| 4,605,306 | 8/1986 | Kaffka et al. | 356/334 |

FOREIGN PATENT DOCUMENTS

| | | |
|---|---|---|
| 0083574 | 7/1983 | European Pat. Off. |
| 2504264 | 10/1982 | France. |

Primary Examiner—F. L. Evans
Attorney, Agent, or Firm—Handal & Morofsky

[57] ABSTRACT

The subject of the invention is a spectroscopic analysis device comprising a light source, a light analyzer comprising an entrance slit, a diffraction grating and at least one exit slit which are disposed along a Rowland circle, and an optical transmission system.

According to the invention, the entrance slit (3) is mounted so as to be displaceable along the Rowland circle (1), on either side of a central position, the optical transmission system comprises a first, fixed part (I) associated with the light source (5; 8) and a second, movable part (II) associated with the entrance slit (3) and mounted so as to be displaceable parallel to itself in a direction ($a_1$, $a_2$; $b_1$, $b_2$; $c_1$, $c_2$) parallel to the tangent (T) to the Rowland circle (1) at the central position of the entrance slit (3), and the device comprises means for controlling the displacement, in synchronism, of the entrance slit (3) along the Rowland circle (1) and of the movable part (II), parallel to the tangent (T), with maintenance of the direction of the optical axis of the assembly.

12 Claims, 4 Drawing Sheets

SPECTROSCOPIC ANALYSIS DEVICE

The present invention relates to the field of optical spectroscopic analysis and is especially applied to the analysis or the useful part of a light source by simultaneous spectrometry.

In a general way, an apparatus for optical spectrometric analysis comprises a light source, of which it is desired to analyze a useful part, and a light analyzer system which may be monochromatic or polychromatic and which comprises an entrance slit, a dispersion means and at least one exit slit, the position of which is dependent upon the wavelength of the light analyzed and which is associated with a detector, for example of the type incorporating a photomultiplier or photodiodes.

The analysis is undertaken by measuring the intensity of the emission lines of the sample at the various wavelengths.

Grating simultaneous spectrographs are in particular known, in which the dispersion of the light is provided by a concave diffraction grating, the entrance slit being placed on a circle referred to as the Rowland circle, which is tangent to the concave surface on which the grating is formed and which has a diameter equal to the radius of curvature of this surface. The monochromatic beams given by the grating converge at points situated on the Rowland circle, and it is thus on this circle that the exit slits are placed, permitting the selection of the wavelengths chosen.

As a general rule, use is made of an optical assembly composed of mirrors or lenses and which transmits the useful light from the light source into the spectrometer through the entrance slit and along the axis passing through the center of the grating and the center of the slit, this taking place so as to represent the image of the useful part of the light source in material form on the entrance slit of the spectrometer.

Such systems permit a fairly rapid analysis, since the measurement of the intensity of all the lines is made simultaneously. However, all the wavelengths are not accessible, since it is possible to measure only those which correspond to the position of the exit slits.

Another difficulty is due to the nature of the light source which is to be analyzed.

A distinction is in fact made between, on the one hand, the direct-excitation sources, where all the emitted light is useful and, on the other hand, the energy-transfer sources, where the useful light is disturbed by the medium in which it is located, for example within a high-frequency-induced plasma. In order to undertake analyses of this second type of light source under the best conditions, it is necessary for only the useful light to be able to be introduced into the spectrometer.

It has been seen that, with polychromatic devices, only the wavelengths which are initially provided are accessible. It is certainly possible to provide for a displacement of the exit slits in order to adjust to other wavelengths, as has been provided, for example, in European Patent No. 0,083,574 published on Jul. 13, 1983 by the same company, but this involves a displacement en bloc of all the slits, which can be implemented only over a small amplitude and gives a simple possibility of adjustment. To the extent that it is necessary to maintain a very great accuracy of positioning of the exit slits on the Rowland circle, it would be difficult to provide for a possibility of individual adjustment of the exit slits without excessively complicating the system.

It is also possible to envisage the displacement of the entrance slit in such a manner as to provide access to other wavelengths by scanning the spectrum. However, in this case, the result is a misalignment of the entrance optical axis of the polychromatic device with the axis of the optical collection device and of the source. Accordingly, such a misalignment cannot normally be tolerated in cases where, as has been indicated previously, the useful light must come from a well-defined location of the source.

The specific object of the invention is to solve such a problem.

According to the invention, a simultaneous displacement is in fact made of the entrance slit and of a part of the optical collection device without modification of the direction of the optical axis; this permits the introduction into the spectrometer of only the useful light rays, as if the entrance slit were fixed, while making an entire range of wavelengths accessible without modification of the position of the exit slits.

Thus, in a general way, the invention is applicable to a spectroscopic analysis device comprising a light source, of which it is desired to analyze a useful part, a light analyzer comprising an entrance slit, a diffraction grating and at least one exit slit associated with a detector, the assembly being disposed along a Rowland circle, and an optical transmission system disposed along an optical axis passing through a useful part of the source, the entrance slit and the center of the grating, and associated with means for selecting the useful light.

According to the invention, the entrance slit is mounted so as to be displaceable along the Rowland circle on either side of a central position and the optical transmission system comprises a first part associated with the useful part of the light source and remaining fixed during the analysis and a second, movable part associated with the entrance slit, and mounted so as to be displaceable parallel to itself in a direction parallel to the tangent to the Rowland circle at the central position of the entrance slit, on either side of a mean position for which the optical axis of the movable part passes through said central position, and the device comprises means for controlling the displacement, in synchronism, of the entrance slit along the Rowland circle and of the movable part parallel to the tangent while maintaining the entrance slit on the optical axis of the assembly.

In fact, irrespective of the position of the slit on the Rowland circle, such an assembly forms the image of the same useful part of the source on the entrance slit and permits the introduction into the spectrometer of the light rays originating from the useful part of the source, while minimizing the useless rays.

In a first embodiment, each part of the optical transmission system is composed of at least one lens, and the movable part comprises a diaphragm which limits the illumination aperture.

In a second embodiment, the two parts of the optical transmission system are each composed of a concave mirror, fixed and movable respectively, the movable mirror being associated with a diaphragm which limits the illumination aperture.

According to a further advantageous arrangement, means for transferring the useful light, for example an optical fiber or a bundle of optical fibers, are interposed between the two parts, fixed and movable respectively, of the optical transmission system. For example, the first part of the optical transmission system is composed of a first, fixed lens associated with the entrance face of at least one optical fiber, while the second part of the optical transmission system is composed of a second, movable lens associated with the exit end of the same optical fiber.

In a particular embodiment of the invention, the means for controlling the displacements, in synchronism, of the entrance slit and of the movable part of the optical transmission system comprise, on the one hand, an arm mounted to rotate about an axis passing through the center of the Rowland circle and perpendicular to its plane and at the end of which there is mounted an element carrying the entrance slit and, on the other hand, an element for supporting the movable part of the optical transmission system comprising a part mounted to slide within a slideway parallel to the direction of the tangent to the Rowland circle at the central position of the slit, the rotary arm and the supporting element being connected by a linkage means capable of causing correspondence between any rotation of the arm causing a shift of the slit perpendicular to the direction of the optical axis of entrance into the collimator and a corresponding displacement of the element for supporting the movable part on its slideway causing a shift of the same amplitude of the optical axis while remaining parallel to itself and conversely.

In a particularly advantageous embodiment, the linkage means between the rotary arm and the element for supporting the movable part is composed of an arm which is displaceable in translation on a fixed slideway in a direction perpendicular to the optical axis of entrance into the polychromatic device and on which there are formed two ground plane shoulders parallel to the optical axis, the rotary arm and the supporting element being each equipped with an index associated with means for the application of said index onto the corresponding shoulder in both directions of displacement of the linkage arm on its slideway.

Further advantages and features of the invention will become evident on reading the description, which follows, of non-limiting embodiments of the spectrometric analysis device according to the invention, with reference to the accompanying drawings, in which:

FIG. 1 shows diagrammatically the entire device comprising the system for the transmission of the light to be analyzed and the analyzer system.

Figure 1:
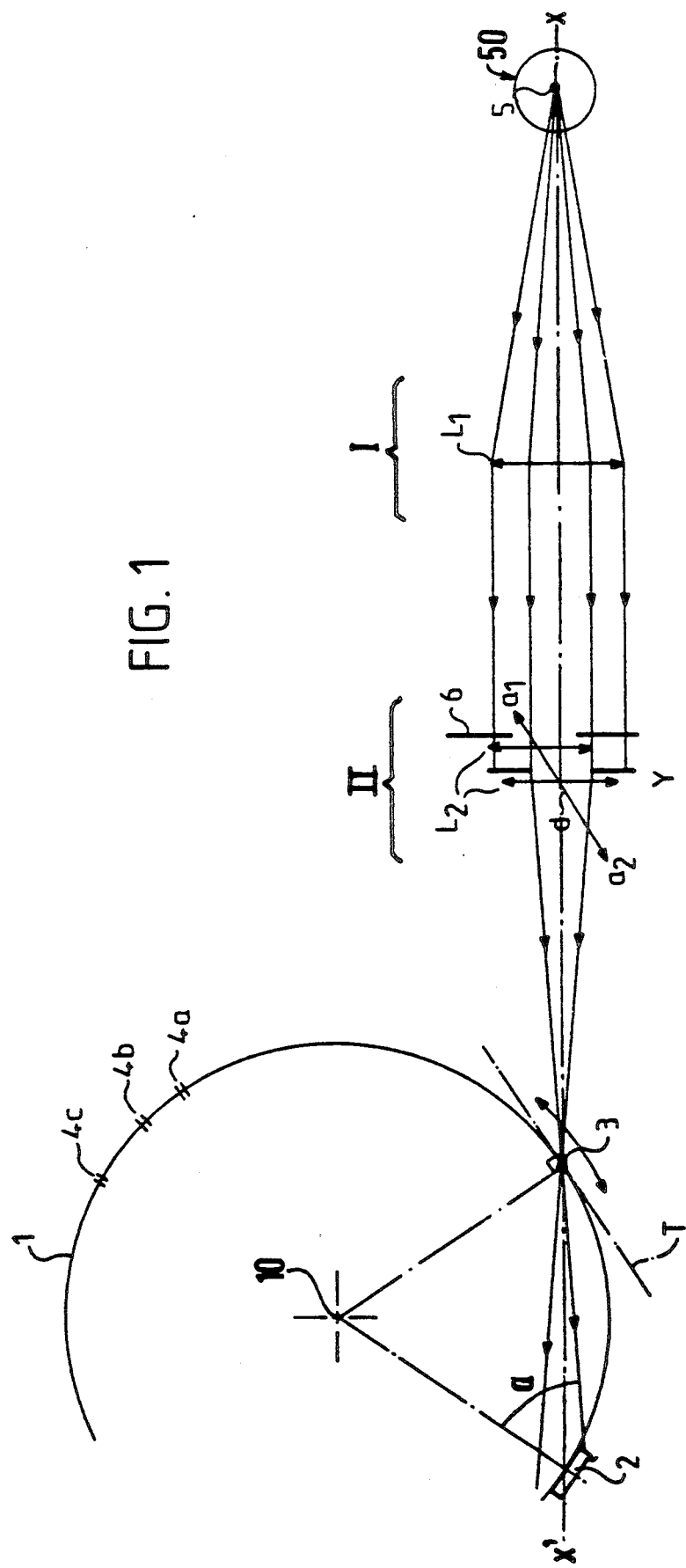
FIGS. 1, 2 and 3 are diagrammatic representations of three embodiments of the device of the invention respectively.

The light analyzer is of the well-known type employing the assembly referred to as a Rowland assembly and does not need to be described in detail. Thus, FIG. 1 shows only the Rowland circle 1 on which there are placed the diffraction grating 2, an entrance slit 3 and one or more fixed exit slits 4a, 4b, 4c.

In the example shown, the light source to be analyzed is placed within a high-frequency-induced plasma 50 which may have, for example, a diameter of 15 to 20 mm over a height of 40 mm, the light to be analyzed being localized within a volume 5 which may have a diameter of 1 to 3 mm and a height of a few millimeters.

The optical system for transmitting the light is composed of a first lens $L_1$ of focal length $f_1$ and a second lens $L_2$ of focal length $f_2$, the ratio of the focal lengths being determined according to the desired enlargement. In FIG. 1, the light source 5 is placed at the object focus of the lens $L_1$ and the entrance slit 3 is placed at the image focus of the lens $L_2$, the rays thus being parallel to the optical axis X'X between the two lenses, but this arrangement is not obligatory and it is sufficient for the beam emitted by the light source 5 to be transformed by the optical system into a beam converging onto the entrance slit 3. Likewise, each lens $L_1$ and $L_2$ may be composed of an assembly of lenses, the optical system comprising, in a general way, two parts I and II. At least one of these two parts, for example the exit part II, comprises a diaphragm 6 which permits the limitation of the useful diameter of the light which illuminates the entrance slit 3, this useful diameter being computed to cover the entire diffraction grating 2.

FIG. 1 corresponds to the initial arrangement of the polychromatic device for which all the elements are aligned along an axis X'X which constitutes the optical axis of the optical transmission system and which passes through the light source 5, through the entrance slit 3 and through the center of the grating 2. In this position, the beam emitted by the source 5 illuminates the grating 2 with an angle of incidence a and is diffracted into a certain number of beams, each corresponding to one wavelength and which converges at various points 4a, 4b, 4c of the Rowland circle at which there are placed the exit slits, each associated with a detector permitting the measurement of the intensity of the corresponding line. For a certain angle of incidence a, each exit slit 4a, 4b, 4c thus corresponds to a precise wavelength.

It is clearly seen in the figure that, in order to modify the wavelengths thus measured or indeed in order to effect an adjustment of the wavelength for example to center the slit on the peak of the line, it is necessary to modify the position either of the grating or of the exit slits, or of the entrance slit 3. Now, the first two solutions involve a certain complication of the device if it is desired to maintain the required accuracy.

For this reason, it is preferred to displace the entrance slit 3 on either side of the central position in such a manner as to modify the angle of incidence a. It is thus possible to cause the convergence, on one or the other of the fixed exit slits, of lines of differing wavelengths, it being possible for the latter to be computed from the position adopted by the entrance slit.

However, it appears that, if the entrance slit 3 is displaced in relation to the central position situated on the axis X'X, it no longer receives the light coming from the point source 5.

Figure 4:
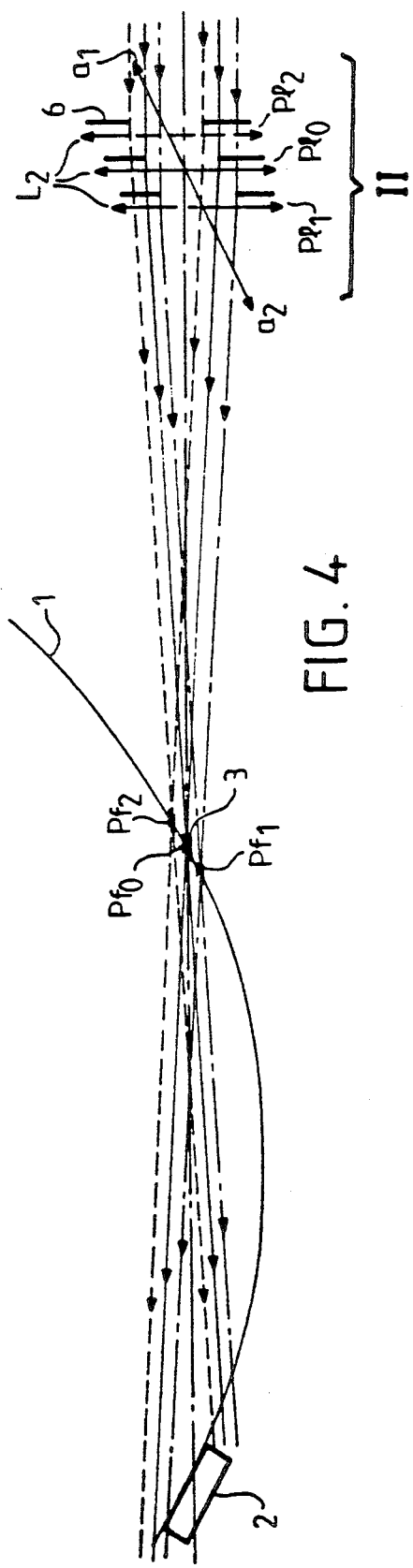
FIG. 4 is an optical diagram showing the paths of the light beam entering the polychromatic device, depending upon the positions of the entrance slit.

The invention permits resolution of this problem by imparting mobility to the exit part II of the optical system and by displacing it by translation in a direction $a_1 a_2$ parallel to the tangent T to the Rowland circle at the central position of the entrance slit 3. In fact, as has been shown in FIG. 4, if the displacement by rotation of the entrance slit 3 is small in relation to the diameter of the Rowland circle 1, the distances are maintained and the defocusing by displacement of the slit 3 which passes from the position $Pf_0$ to one of the positions $Pf_1$ or $Pf_2$, is compensated by the corresponding displacement of the lens $L_2$ which itself passes from the position $Pl_0$ to one of the positions $Pl_1$ or $Pl_2$. The useful diameter of the lens $L_2$, which diameter is limited by the diaphragm 6, is computed to cover the entire grating, irrespective of the position of the entrance slit. The useful diameter of the entrance lens $L_1$ must thus be equal, as a minimum, to the useful diameter of $L_2$ limited by the diaphragm 6, to which is added the shift of the slit according to the component (Y) perpendicular to the optical axis X'X.

Moreover, the shifts of the entrance slit 3 and of the lens. $L_2$ according to the component (Y) must be strictly of the same amplitude in relation to the central axis X'X defined by the alignment between the center of the grating 2, the central position of the slit 3, the centers of the lenses $L_2$ and $L_1$ and the useful zone of the source 5. A device permitting this result to be obtained is shown, diagrammatically by way of example, in FIG. 5 and will be described hereinbelow.

In the embodiment shown in FIG. 2, there is again found the same configuration of the exit slits 4a, 4b, 4c and of the slit 3 on the Rowland circle 1 defined on the basis of its center 0 and of the diffraction grating 2, but the lenses $L_1$ and $L_2$ are replaced respectively by concave mirrors $M_1$ and $M_2$. These mirrors $M_1$ and $M_2$, being concave, are of the spherical or parabolic type and have focal lengths which are identical or alternatively in a specified ratio as a function of the desired magnification. The mirror $M_1$ is fixed and integral with the source 5, while the mirror $M_2$ may be displaced on an axis $b_1$-$b_2$ which is parallel to the tangent T to the Rowland circle at the mid-point of the displacement of said entrance slit 3 on the Rowland circle 1. The source 5 and the entrance slit 3 of the polychromatic device are placed respectively at the foci of the mirrors $M_1$ and $M_2$.

The mirror $M_1$ transforms the diverging rays from the useful zone of the plasma source 5 into parallel beams, while the mirror $M_2$ transforms these parallel rays into a beam converging onto the entrance slit in order to represent thereat in material form the image of the useful zone of the plasma source 5. Under these conditions, irrespective of the position of the entrance slit 3 on the Rowland circle 1, the grating 2 is illuminated by the rays originating from the same useful zone of the source 5, and the defocusing by displacement of the slit 3 is compensated by the displacement of the mirror $M_2$, as specified hereinabove.

The useful dimensions of the mirror $M_2$, which are limited by the diaphragm 7, are computed to cover the entire grating 2, irrespective of the position of the entrance slit 3. Moreover, the dimensions of the mirror $M_1$ must be sufficient for the rays of the parallel beam to cover the mirror $M_2$ completely, irrespective of the position of the latter in its displacements along the axis $b_1$-$b_2$. Moreover, the displacement of the entrance slit 3 and of the mirror $M_2$ according to the component Y must be strictly of the same amplitude in relation to the central axis defined by the alignment of the grating 2, of the slit 3 and of the center of the mirror $M_2$, this axis remaining strictly parallel to the axis passing through the plasma source 5 and the center of the mirror $M_1$.

In the two embodiments which have just been described, the displacement of the movable part II parallel to itself does not destroy the collimation effect on the entrance slit 3, on account of the fact that the latter is placed substantially at the image focus of the movable part II, while the source 5 is placed at the object focus of the fixed part I. However, such an arrangement is not essential; the characteristics of the optical systems permitting the achievement in some other way of the displacement of a part of the system with maintenance of the optical axis parallel to itself.

Figure 3:
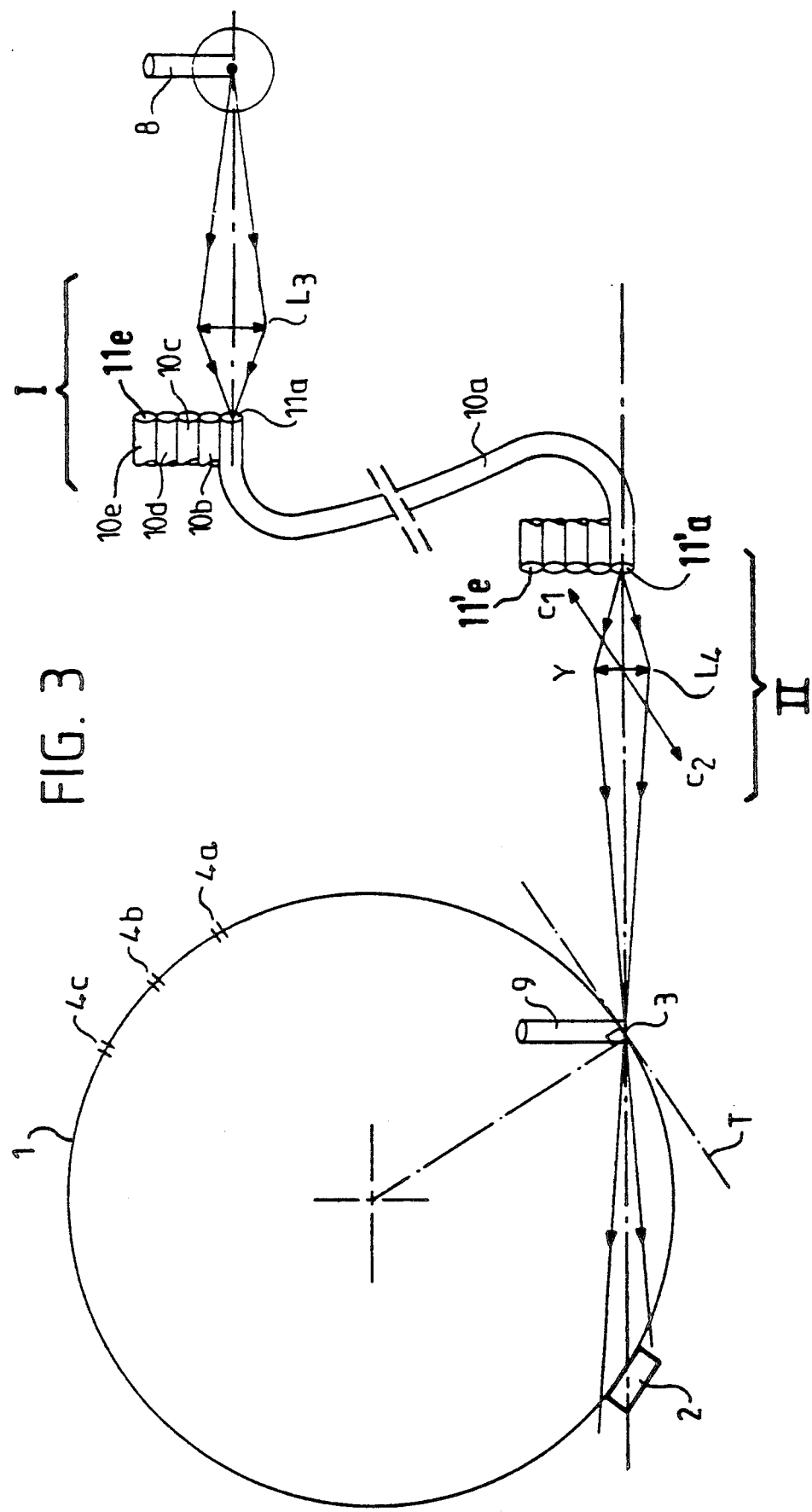

It is possible, for example, to use another particularly advantageous arrangement shown in FIG. 3 and in which the transfer of the light between the fixed part I and the movable part II is effected by means of one or more optical fibers 10.

In fact, the useful part to be analyzed of the light source is not generally in the form of a point and may be present in the form of a small cylinder having a height of several millimeters and which is oriented in such a manner as to be parallel to the entrance slit 3 and to the exit slits 4a, 4b, 4c, that is to say perpendicular to the plane of the Rowland circle.

In this case, use will advantageously be made of a bundle of optical fibers 10a, 10b, 10c . . . , the entrance faces 11 and the exit faces 11' of which will be superposed in the same direction perpendicular to the plane of the Rowland circle.

The first part I of the optical transmission system, represented in the figure by the lens $L_3$, represents in material form the image of the cylinder 8 constituting the light source on all the entrance faces 11a . . . 11e of the optical fibers 10a . . . 10e. This image is transmitted by all the optical fibers to the ends 11'a . . . 11'e from which it is represented i material form at 9 on the entrance slit 3 by the lens $L_4$ constituting the movable part II of the optical system.

Thus, the flexibility of the optical fibers permits the displacement of the movable part II with the exit ends 11'a to 11'e parallel to the tangent T to the Rowland circle and while maintaining the direction of the optical axis.

As previously, the displacement of the entrance slit 3 and of the assembly composed of the lens $L_4$ and the exit end 11b of the optical fiber 10a according to the component Y must be strictly of the same amplitude in relation to the central axis defined by the alignment of the grating 2, of the entrance slit 3, of the center of the lens $L_4$ and of the center of the optical fiber 10a.

In summary, while the displacement of the entrance slit 3 on the Rowland circle 1 permits the maintenance of the focal length of the spectrometer, the associated displacement of the lens II, as has just been described, permits the maintenance of the alignment of the spectrometer in front of the useful part 5 of the source, and this takes place even for amplitudes of displacement of the entrance slit 3 of several millimeters, or even several tens of millimeters, without this displacement affecting substantially the characteristics of the emission lines to be analyzed.

Thus, in the case of a polychromatic device having a focal length of 500 mm, equipped with a 3600 lines/mm grating, a displacement of +8 mm corresponding to a wavelength scanning of +2.2 mm, the signal from the lines to be analyzed is maintained and the signal/background ratio is maintained. As a result of this, the detection limits specific to the emission line are maintained.

Figure 5:
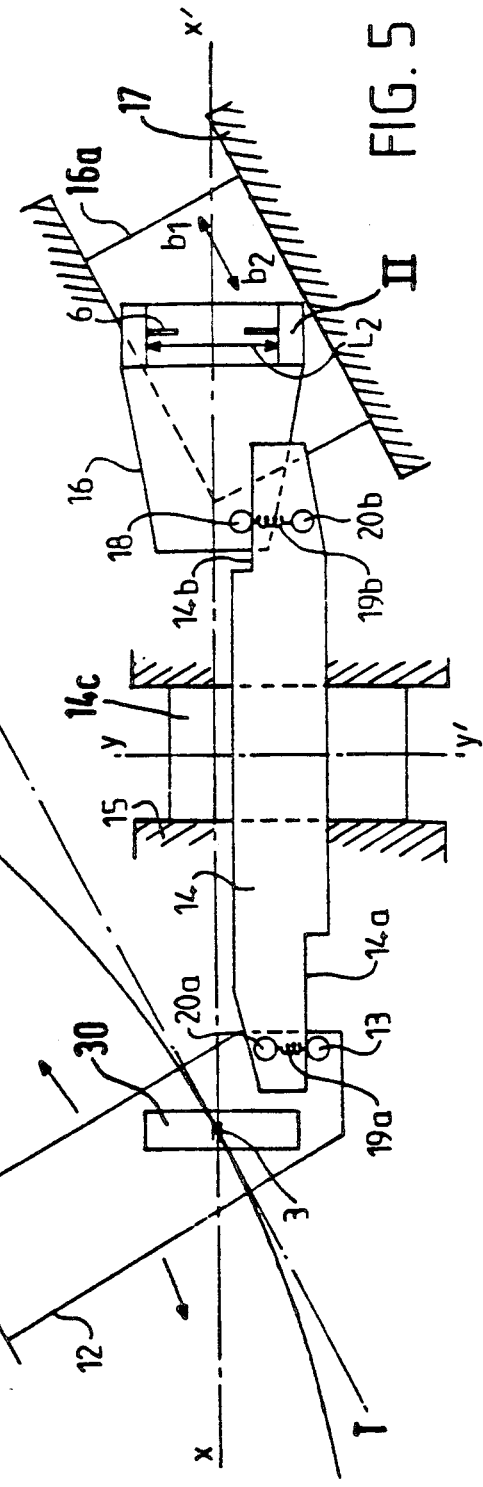
FIG. 5 is a diagrammatic representation of a drive mechanism permitting the simultaneous displacement of the slit and of the movable part.

FIG. 5 shows, by way of example, a mechanical system permitting the linking of the displacements of the entrance slit 3 to the displacement of the movable part 2, and conversely, while maintaining the same amplitude of the lateral shift in the direction Y'Y perpendicular to the optical axis X'X.

Figure 2:
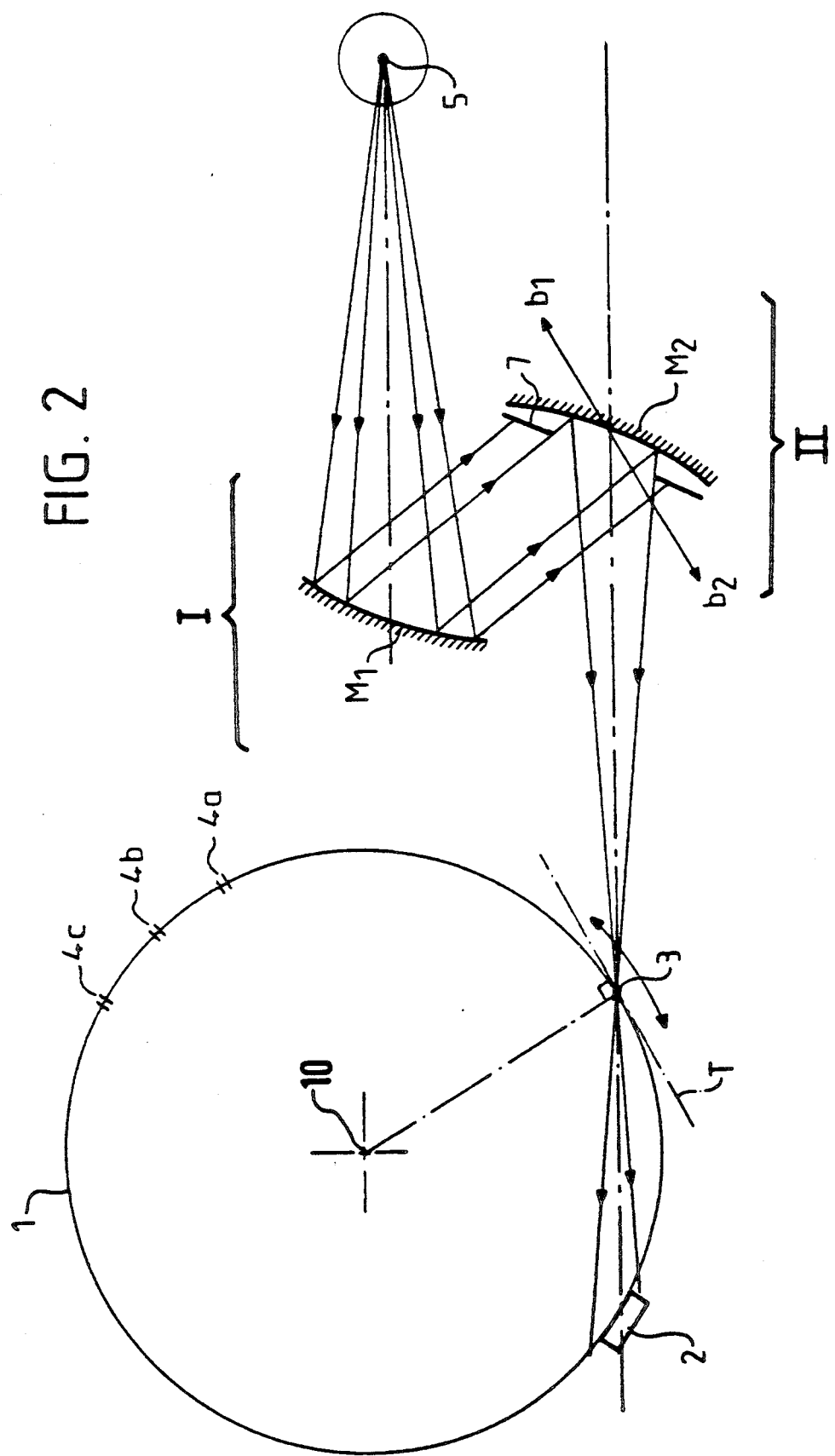

The device shown may be matched, in any particular way, to the three embodiments provided in FIGS. 1, 2 and 3.

The entrance slit 3 is formed on a support 30 which is mounted at the end of an arm 12 mounted to rotate about the axis 10 passing through the center of the Rowland circle 1 and perpendicular to its plane. A rotation of the arm 12, for example by means of a motor (not shown), thus permits the displacement of the slit 3 along the circle 1 on either side of a central position.

Moreover, the movable part 2 of the optical system, for example the lens $L_2$ associated with the diaphragm 6, is mounted on a supporting element 16 which is fixed on a part 16a mounted to slide in translation along a slideway 17 defining a translation axis $b_1$ $b_2$ parallel to the tangent T to the Rowland circle at the central point of displacement of the slit 3.

Between the rotary arm 12 and the supporting element 16 there is placed a linkage arm 14 which is itself mounted on a part 14c which can slide along a slideway 15 in a direction Y'Y perpendicular to the optical axis X'X' of the polychromatic device. The arm 14 extends between the two parts 12 and 16 and is equipped, at the location of each one of them, with two shoulders, 14a and 14b respectively, which are ground in such a manner as each to define a plane perpendicular to the plane of the Rowland circle and parallel to the optical axis X'X.

The rotary arm 12 is equipped with an index 13 which is applied against the plane shoulder 14a, for example by a spring 19a fastened to a stub 20a.

In the same way, the sliding element 16 is equipped with an index 18 which is applied against the plane shoulder 14b by a spring 19b fastened to a stub 20b.

Under these conditions, any displacement by rotation of the arm 12 about its axis causes, through the index 13, a corresponding displacement of the arm 14 which initiates, in its turn, by means of the shoulder 14b and the stub 18, a displacement by translation of the supporting element 16 corresponding to a lateral shift of the same amplitude in the direction Y'Y. Conversely, a displacement of the sliding element 16 would cause a rotation of the arm 12 corresponding to a lateral shift of the same amplitude parallel to the direction Y'Y. Thus, for the adjustment of the detected wavelength, it is possible to act either on the entrance slit 3, by means of the rotary arm 12, or on the position of the movable part 2 of the optical system.

The invention is not, of course, limited to the details of the various embodiments which have just been described, it being possible for other equivalent arrangements to be devised by relying upon other optical or mechanical arrangements permitting, in a general way, the formation of the image of the same useful part of the source on the entrance slit in order to introduce into the spectrometer the light rays originating from the useful part of the source, minimizing the useless rays, this taking place irrespective of the position of the entrance slit on the Rowland circle.

In this way, the synchronized displacements of the entrance slit and of the optical system could be controlled by motors acting separately on the rotary arm 12 and on the sliding element 16 and connected together by a synchronizing means of known type.

Moreover, the invention has been described in the case where analysis takes place of one and the same useful part of the light source, the first part I of the entrance optical device being fixed. However, the device may also be employed, as appropriate, for the analysis of a source possessing a plurality of useful parts. In this case, the part I of the optical device could be displaced according to a plane perpendicular to the optical axis in such a manner as to sample successively rays originating from the various useful parts of the source in order to analyze them, said part I remaining fixed during the analysis of the useful part chosen.

For example, in the case of analyses by inductive coupling plasma (ICP), the emission height varies as a function of the lines and of the elements. The vertical displacement of the first part I (lens, mirror or fiber arrangement) would permit an optimal sampling of the analysis signals for each one of the elements.

Thus, the invention provides a solution to the problem of access to an entire range of wavelengths of one or more useful parts of a light source by virtue of a displacement of the entrance slit of the polychromatic device, the exit slits being fixed, by introducing exclusively into the light analyzer the useful light rays originating from the useful part of the source to be analyzed, and by minimizing the others in the same manner as if the entrance slit of the polychromatic device had remained fixed.

It is thus possible, with a small number of detectors, to cover all the elements to be analyzed which are contained within a source. Proceeding from a polychromatic device having a small number of lines, the invention permits an increase in the number of lines analyzed to be achieved.

The invention likewise facilitates the quantitative analysis of a sample, since it is possible, by a small scan, to gain access very rapidly to all the lines while using the minimum of samples; this is of particular benefit in biology.

What is claimed is:

1. A spectrometric analysis device comprising a light source of which it is desired to analyze a useful part, a light analyzer comprising an assembly of an entrance slit, a diffraction grating and at least one exit slit associated with a detector, the assembly being disposed along a Rowland circle, and an optical transmission system, disposed along an optical axis passing through a useful part of the source, the entrance slit and the center of the grating and associated with means for selecting the useful light, wherein the entrance slit (3) is mounted so as to be displaceable along the Rowland circle (1), on either side of a central position, wherein the optical transmission system comprises a first part (I) associated with the useful part of the light source (5; 8) and remaining fixed during the analysis of said useful part and a second, movable part (II) associated with the entrance slit (3) and mounted so as to be displaceable parallel to itself in a direction ($a_1$, $a_2$; $b_1$, $b_2$; $c_1$, $c_2$) parallel to the tangent (T) to the Rowland circle (1) at the central position of the entrance slit (3), on either side of a mean position for which the optical axis of said movable part (II) passes through said central position, and wherein the device comprises means for controlling the displacements, in synchronism, of the entrance slit (3) along the Rowland circle (1) and of the movable part (II), parallel to the tangent (T) with maintenance of the direction parallel to itself.

2. The spectrometric analysis device as claimed in claim 1, wherein the fixed part (I) and the movable part (II) of the optical transmission system are composed respectively of at least one fixed ($L_1$) and movable ($L_2$) lens respectively, the movable lens ($L_2$) being associated with a diaphragm (6) for the isolation of the useful part of the light.

3. The spectrometric analysis device as claimed in claim 1, wherein the two parts of the optical transmission system are composed respectively of a fixed concave mirror ($M_1$) and a movable concave mirror ($M_2$), at least the movable mirror ($M_2$) being associated with a diaphragm (7).

4. The spectrometric analysis device as claimed in claim 3, wherein the concave mirrors are selected from a group consisting of spherical and parabolic concave mirrors.

5. The spectrometric analysis device as claimed in claim 1, wherein, between the first, fixed part of the optical transmission system ($L_3$, 11a) and the second, movable part ($L_4$, 11b) of the optical transmission system there are provided optical fiber means for the transfer of the useful light.

6. The spectrometric analysis device as claimed in claim 1, wherein the first part of the optical transmission system is composed of a first, fixed lens ($L_3$) associated with the entrance face (11a) of at least one optical fiber (10a), while the second part of the optical transmission system is composed of a second, movable lens ($L_4$) associated with the exit end (11b) of said optical fiber (10a).

7. The analysis device as claimed in one of the preceding claims, wherein the means for controlling the displacements, in synchronism, of the entrance slit (3) and of the movable part (II) of the transmission system comprise:

an arm (12) mounted to rotate about an axis (10) passing through the center of the Rowland circle and perpendicular to its plane and at the end of which there is mounted an element (30) carrying the entrance slit (3), an element (16) for supporting the movable part (II) of the optical transmission system, comprising a part (16a) mounted to slide in a slideway (17) parallel to the direction of the tangent to the Rowland circle at the central position of the slit (3), a linkage means (14) between the rotary arm (12) and the supporting element (16) causing correspondence between any rotation of the arm (12) causing a displacement of the slit (3), perpendicular to the direction of the optical axis (X'X) of entrance into the analysis device and a corresponding displacement of the element (16) for supporting the movable part (II) on its slideway causing a displacement of the same amplitude of the optical axis (X'X) parallel to itself, and conversely.

8. The analysis device as claimed in claim 7, wherein the linkage means (14) is composed of an arm (14) displaceable in translation on a slideway (15) in a direction (Y'Y) perpendicular to the optical axis (X'X) of entrance into the analysis device and on which there are formed two ground plane shoulders (14a, 14b) parallel to the optical axis (X'X), the rotary arm (12) and the supporting element (16) being each equipped with an index, (13) (18) respectively, and associated with means (19a, 20a) (19b, 20b) respectively for the application of each index (13) (18) onto the corresponding shoulder (14a) (14b) in both directions of displacement of the linkage arm (14) on its slideway (15).

9. The analysis device as claimed in claim 8, wherein the means for the application of the two indices (13) (18) are springs (19a) (19b) constantly urging each index (13; 18) to bear respectively against the corresponding shoulder (14a) (14b) of the arm (14).

10. The analysis device as claimed in claim 1, wherein the displacement of the entrance slit (3) along the Rowland circle, as well as the corresponding displacement of the movable part II, may reach a plurality of tens of millimeters.

11. The analysis device as claimed in claim 1, wherein, in the case of a light source comprising a plurality of useful parts, the first part (I) may be displaced in a plane perpendicular to the optical axis in such a manner as to sample rays originating from another useful part, said first part (I) remaining fixed during the analysis of the useful part chosen.

12. A spectrometric analysis device comprising:
(a) a light source a useful part of the light from which is to be analyzed;
(b) means to select useful light from the source for analysis;
(c) a light analyzer including an assembly of an entrance slit, a diffraction grating and at least one exit slit associated with a detector, said entrance and exit slits and said diffraction grating being disposed on the Rowland circle defined by said grating; and
(d) an optical transmission system comprising:
  (i) a first, source part to receive light from said light source which first, source part is disposed along a first optical axis passing through said light source and
  (ii) a second, exit part to transmit light to said light analyzer which second, exit part is disposed along a second optical axis passing through said entrance slit and the center of said grating;

wherein the entrance slit is mounted to be displaceable along the Rowland circle on either side of a central position, and wherein said second part of the optical transmission system is displaceably mounted for movement in a direction parallel to a tangent to the Rowland circle at said central position of the entrance slit, said movement of said second part of the optical transmission system extending on either side of a mean position of said second part in which the second optical axis passes through said central position of the entrance slit, and wherein further said light analyzer device comprises means for controlling the displacements, in synchronism, of the entrance slit along the Rowland circle and of the movable second part parallel to the tangent while maintaining said second optical axis parallel to its disposition in said mean position.

* * * * *